US00PP08082P

United States Patent [19]

Lyrene

[11] Patent Number: Plant 8,082

[45] Date of Patent: Jan. 5, 1993

[54] RABBITEYE BLUEBERRY CULTIVAR SNOWFLAKE

[75] Inventor: Paul M. Lyrene, Gainesville, Fla.

[73] Assignee: University of Florida Research Foundation, Inc., Gainesville, Fla.

[21] Appl. No.: 639,624

[22] Filed: Jan. 10, 1991

[51] Int. Cl.[5] ..... A01H 5/00

[52] U.S. Cl. ..... Plt./33.1

[58] Field of Search ..... Plt. 33, 33.1

[56] References Cited

U.S. PATENT DOCUMENTS

P.P. 6,701 3/1989 Wood ..... Plt. 33

*Primary Examiner*—James R. Feyrer

*Attorney, Agent, or Firm*—Saliwanchik & Saliwanchik

[57] ABSTRACT

Description and specifications of a new and distinct rabbiteye blueberry variety which originated from seed produced by a hand-pollinated cross of Florida K and NC 1830 is provided. The new rabbiteye blueberry variety can be distinguished from all others by its low chilling requirement and its combination of late flowering with early ripening.

1 Drawing Sheet

SUMMARY OF THE INVENTION

The new and distinct variety of rabbiteye blueberry originated from a hand pollinated cross of Florida - K×NC 1830 made in 1981 at the Florida Agricultural Experiment Station experimental blueberry greenhouse in Gainesville, Fla. The seeds resulting from this controlled hybridization were germinated in a greenhouse during the winter of 1981–1982. Resulting seedlings were planted in the spring of 1982 in a field on the University of Florida Horticultural Unit at Gainesville Fla. The seedlings fruited in the spring of 1984 and one, designated FL 84-106, was selected for its outstanding fruit quality and early ripening, as compared to other known varieties.

During 1984, the original plant selection was propagated asexually by rooting softwood cuttings, and a test planting of 15 plants was established. Other rooted cuttings of this clone have been grown in the University of Florida blueberry breeding greenhouse to obtain information on fertility and fruit quality under greenhouse conditions.

The new variety has been asexually propagated on at least three other occasions by softwood cuttings. It roots readily from softwood cuttings and grows well in the cutting nursery. In all cases in which the clone has been propagated by cuttings, the vegetative and fruit characteristics of the original plant have been maintained.

Bushes of the new variety are vigorous and upright in growth. Plants set on a soil of intermediate fertility were 170 cm after five years. Sprouts from the plants were arising from a band 120 cm wide from six-year old plants and the drip line of the canopy was 220 cm wide. The plant produces basal shoots in sufficient quantities to renew the plant as it grows. Because Snowflake prolifically sprouts from the base by means of rhizome budding, pruning or mowing will be needed to maintain the narrow base necessary for mechanical harvesting. After six to eight years, top hedging or selective cane removal is needed to prevent excessive plant height. The number of flower buds produced is about average for rabbiteye blueberry cultivars and is sufficient to produce a heavy crop. Plants of the new variety flower one week before they produce new leaves in the spring, and foliation has always been excellent.

Plants of the new variety appear to be above average for a rabbiteye blueberry in tolerance to Phytophthora root rot. Neither cane canker, incited by *Botryosphaeria corticus*, nor stem blight, incited by *Botryosphaeria dothedia*, has been a problem in the field plantings. Resistance to Botrytis blight, incited by *Botrytis cinerea*, has been equal to or greater than that of most other rabbiteye cultivars planted in the same test field. Leaf retention is good in the fall, indicating satisfactory levels of tolerance to the various species of defoliating fungal pathogens prevalent in the experimental area.

The new variety has a low chilling requirement, and has not shown delayed flowering of leafing in Gainesville, Fla. following winters with 300 total hours with temperatures below 7° C. On the other hand, the variety tends to hold its dormancy well during warm periods during the winter, and is thus less prone to spring frost damage than other early-ripening rabbiteye blueberry varieties. The fruit ripen exceptionally early for a rabbiteye blueberry, due to a very short flowering-to-ripening interval. Ripening date averages 10 days earlier than Beckyblue, which is the earliest-ripening rabbiteye cultivar now available, and 15 days earlier than Climax, another rabbiteye variety widely grown because of its early ripening. Yet, the average date of full bloom for the new variety is more than two weeks later than for Beckyblue and more than one week later than Climax. The average date of first commercial harvest on plants of the new variety grown in north central Florida will be about May 10, and midharvest will be about May 18. Harvest dates are about ten days later than for the highbush variety Marimba. Varieties recommended for crosspollination of Snowflake include Climax, Brightwell, Woodward, and Bluebelle.

Fruit of the new variety are large, dark-blue in color, and possess a moderately heavy surface wax. Firmness is medium to poor, a characteristic which will make this variety best suited to local marketing. The stem scar is medium in size, and the flavor is good and similar to that of the major rabbiteye varieties. Seediness and skin thickness are about average for a rabbiteye blueberry cultivar. The fruit detach readily from the plant when ripe, and are easy to harvest by hand.

Windy has 72 chromosomes in each somatic cell and is distinguished from Marimba which has 48 chromosomes in each somatic cell.

The new variety has been named the SNOWFLAKE cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blueberry clone. Where dimensions, sizes, colors, and other characteristics are given, it is to be understood that such characteristics are approximations of averages set forth as accurately as practicable.

The description reported herein is from specimens grown in Gainesville, Fla.

Plant:

*Size.*—Medium 170 cm tall and sprouting from a base 120 cm in a diameter after five years in field plots.

*Time of* 50% *anthesis.*—March 6.

*Growth.*—Medium to high vigor, cessation of growth in early October. Plant more upright than spreading.

*Productivity.*—Medium to high. Young plants precocious.

*Cold hardiness.*—Plant and dormant flower buds hardy to below −13° C. Flowers and fruits hardy to −2° C.

*Chilling requirement.*—The plant requires only 300 hours duration of temperatures at or below 7° C. to induce normal leafing and flowering in the spring.

*Stems.*—Moderately upright. Readily produces new sprouts from rhizomes. On five-year old plants growing in the field, length of the terminal growth in one season is 25 cm for mature stems and 80 cm for renewal stems.

*Internode length.*—1.2 cm. Color of 1-year-old stems — red pink (10A, Plate 13 in Maerz, A. and M. R. Paul (1950) "A Dictionary of Color", 2d Ed.).

*Disease resistance.*—Moderate resistance to Phytophthora root rot, stem blight, powdery mildew, Botrytis flower blight, and various defoliating leaf diseases. High resistance to cane canker.

Foliage:

*Leaves.*—Color — mature leaves green (9C, Plate 25, Dictionary of Color, supra). Leaf margins serrulate. Leaves glabrous except for a very few stalked glands on lower surface. Leaves average 34 mm wide × 56 mm long.

Flowers:

*Date of* 50% *anthesis.*—March 6.

*Flower color.*—White.

*Flower shape.*—Urceolate Mean corolla length: 9 mm; width: 7 mm; mean diameter of corolla tube aperture: 3 mm.

*Flower bud number.*—Medium to high. Mean number of flowers per cluster— 10.

The variety is highly self-incompatible.

Fruit:

*Maturity.*—First harvest May 10. Mid harvest May 18.

*Size of berry.*—Medium large. Average weight 1.70 g. Calyx cup 4 mm deep. Berry averages 12 mm tall and 13 mm in diameter.

*Berry color.*—Dark blue (6A, Plate 48, Dictionary of Color, supra), with moderate surface wax.

*Fruit stem scar.*—Medium to good.

*Berry firmness.*—Poor to medium. Firmer than berries from cultivar Woodard; similar in firmness to cultivar Premier.

*Berry flavor and texture.*—Flavor sweet with moderate acid level. Skins of normal thickness and seeds of normal size and number for rabbiteye cultivars.

*Storage quality.*—Medium.

*Uses.*—Primarily for customer-pick and local markets. Also suitable for processing.

*Suitability for mechanical harvest.*—Low due to the lack of berry firmness.

The Variety

The most distinctive feature of the variety is its combination of early ripening and late flowering. The variety flowers more than 2 weeks later but ripens 10 days earlier than the earliest-ripening rabbiteye blueberry variety now available. It produces a high-quality fruit that are suitabe for customer-pick and local markets.

I claim:

1. A new and distinct variety of rabbiteye blueberry plant, substantially as illustrated and described, characterized by its late flowering, early ripening, vigorous, disease-resistant bush, and low chilling requirement.

* * * * *

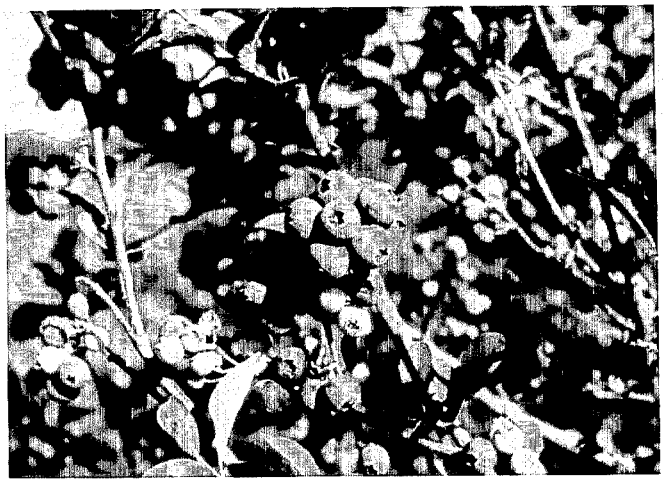
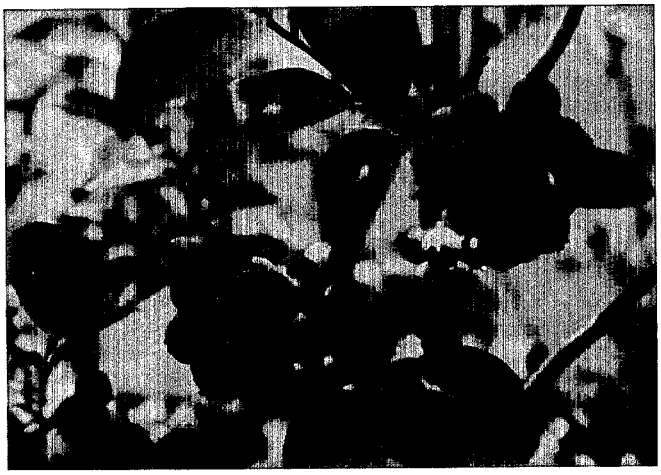

UNITED STATES PATENT AND TRADEMARK OFFICE

CERTIFICATE OF CORRECTION

PATENT NO. : Plant 8,082

DATED : January 5, 1993

INVENTOR(S) : Paul S. Lyrene

It is certified that error appears in the above-identified patent and that said Letters Patent is hereby corrected as shown below:

Column 2: line 15: "of leafing" should read --or leafing--; line 35: "crosspollination" should read --cross-pollination--.

Signed and Sealed this

Twenty-third Day of November, 1993

*Attest:*

*Attesting Officer*

BRUCE LEHMAN

*Commissioner of Patents and Trademarks*